(12) United States Patent
Price

(10) Patent No.: US 7,888,500 B2
(45) Date of Patent: Feb. 15, 2011

(54) PREPARATION AND USES OF LOCKED-RING SUGAR C-GLYCOSIDE DERIVATIVES

(75) Inventor: Neil P. Price, Edelstein, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 197 days.

(21) Appl. No.: 11/899,180

(22) Filed: Sep. 5, 2007

(65) Prior Publication Data

US 2008/0081905 A1    Apr. 3, 2008

Related U.S. Application Data

(60) Provisional application No. 60/848,775, filed on Oct. 2, 2006.

(51) Int. Cl.
| C07H 1/00 | (2006.01) |
| C07H 7/02 | (2006.01) |
| C07H 3/02 | (2006.01) |

(52) U.S. Cl. .................. 536/124; 536/55.3; 514/23
(58) Field of Classification Search .............. 536/124, 536/55.3; 514/23
See application file for complete search history.

(56) References Cited

U.S. PATENT DOCUMENTS 6,075,134 A * 6/2000 Bertozzi et al. ............ 536/17.2
7,049,300 B2 * 5/2006 Dalko et al. ................... 514/23
2004/0048785 A1    3/2004 Dalko et al.
2008/0153760 A1    6/2008 Leroy et al.

OTHER PUBLICATIONS

Rodrigues et al. (Chem. Commun., 2000, 2049-2050).*
Lee et al.(Organic Letters (2005) vol. 7, No. 19, 4269-4272).*
Cervigini et al. (Angew. Chem. Int. Ed. Engl.1996, 35. No. 11).5.*
Riemann, Ingo, et al., "C-Glycosides by Aqueous Condensation of B-Dicarbonyl Compounds with Unprotected Sugers", Australian Jrnl of Chemistry, CSIRO Publ,55,2002,pp. 147-154.
Rodrigues, Filipe, et al., "A convenient, one-step, synthesis of B-C-glycosidic ketones in aqueous media", Chem Commun., 2000, p. 2049-2050.

* cited by examiner

*Primary Examiner*—Shaojia Anna Jiang
*Assistant Examiner*—Michael C Henry
(74) *Attorney, Agent, or Firm*—Randall E. Deck; John Fado; Lesley Shaw

(57) ABSTRACT

"Locked-ring" C-glycoside derivatives may be prepared wherein the ring of the sugar molecule remains intact without the need for any protecting groups. These C-glycoside derivatives may be produced by first reacting an aldose reducing sugar, which may be a hexose or a pentose, with a β-diketone to form a C-glycoside ketone. The C-glycoside ketone is then reacted with a ketone reactive compound, such as a hydrazine or hydroxylamine, optionally linked to a detectable label, to form a C-glycoside derivative wherein the ketone reactive compound is conjugated to the C-glycoside at the site of the ketone. The aldose reducing sugar used in the first reaction may a simple pentose or hexose monosaccharide, or it may be optionally substituted.

13 Claims, 5 Drawing Sheets

PREPARATION AND USES OF LOCKED-RING SUGAR C-GLYCOSIDE DERIVATIVES

This application claims the benefit under 35 U.S.C. 1.19(e) of U.S. provisional No. 60/848,775, filed Oct. 2, 2006, the contents of which are incorporated by reference herein.

BACKGROUND OF THE INVENTION

1. Field of the Invention

This invention relates to a novel process for producing derivatives of C-glycosides wherein the integrity of the ring structure of the sugar is retained.

2. Description of the Prior Art

Numerous techniques for the derivatization of sugars have been described. Such techniques have included reductive amination and the formation of reducing sugar hydrazones, osazones, and oximes. However, in these techniques the integrity of the ring of the sugar is not retained but it is opened. The need therefore remains for improved process for preparing sugar derivatives wherein the ring of the sugar is not opened.

SUMMARY OF THE INVENTION

We have discovered that "locked-ring" C-glycoside derivatives may be prepared wherein the ring of the sugar molecule remains intact without the need for any protecting groups. Surprisingly, C glycoside derivatives may be produced by first reacting an aldose reducing sugar, which may be a hexose or a pentose, with a β-diketone under conditions and for a period of time effective to form a C-glycoside ketone. The C-glycoside ketone is then reacted with a ketone reactive compound, such as a hydrazine or hydroxylamine, optionally linked to a detectable label, under conditions and for a period of time effective to form a C-glycoside derivative wherein the ketone reactive compound is conjugated to the C-glycoside at the site of the ketone. Unlike previous derivatization reactions, the ring structure of the terminal reducing sugar remains intact. The aldose reducing sugar reactant of the first reaction may a simple pentose or hexose monosaccharide, or it may be optionally substituted, at one or more of the C2, C3, C4, C5, and C6 positions in the case of a hexose, or at one or more of the C2, C3, C4, and C5 positions in the case of a pentose.

In accordance with this discovery, it is an object of this invention to provide a process for making C-glycoside derivatives wherein the ring structure of the sugar is not opened.

Another object of this invention to provide a process for making C-glycoside derivatives wherein the ring structure of the sugar is retained without using any sugar protecting groups.

Yet another object of this invention to provide a process for making C-glycoside derivatives in an aqueous solvent, at relatively mild temperatures, and which is nearly quantitative.

Still another object of this invention to provide a process for making C-glycoside derivatives from sugars containing labile groups without alteration or loss of the labile groups.

A still further object of this invention to provide a process for making C-glycoside derivatives wherein the antigenicity of the parent sugar is substantially retained.

Other objects and advantages of the invention will become readily apparent from the ensuing description.

BRIEF DESCRIPTION OF THE DRAWINGS

In FIG. 2A (top), the two peaks at retention time (Rt) 5.98 min and 6.08 min assigned from the electron impact (EI) mass spectra as peracetylated alpha- and beta-glucose. These arise from Rings I and II of acarbose (See Example 1 for ring numbering nomenclature). In FIG. 2B (lower) the two peaks at Rt 5.93 min and 6.06 min assigned as peracetylated alpha- and beta-glucose from glucose Ring II, and a third peak at Rt 7.39 min assigned as glucose-C-ketoglycoside arising from Ring Ia. The latter peak (Rt 7.39 min) gave rise to a EI-MS spectrum composed of four major ions m/z 153, 166, 195, and 198, that are characteristic for peracetylated glucose-C-ketoglycoside (Price, N P, Momany, F A, Adeuya, A, J Mass Spectrom., 2007 Aug. 13, [Epub ahead of print]).

DETAILED DESCRIPTION OF THE INVENTION

Figure 1:
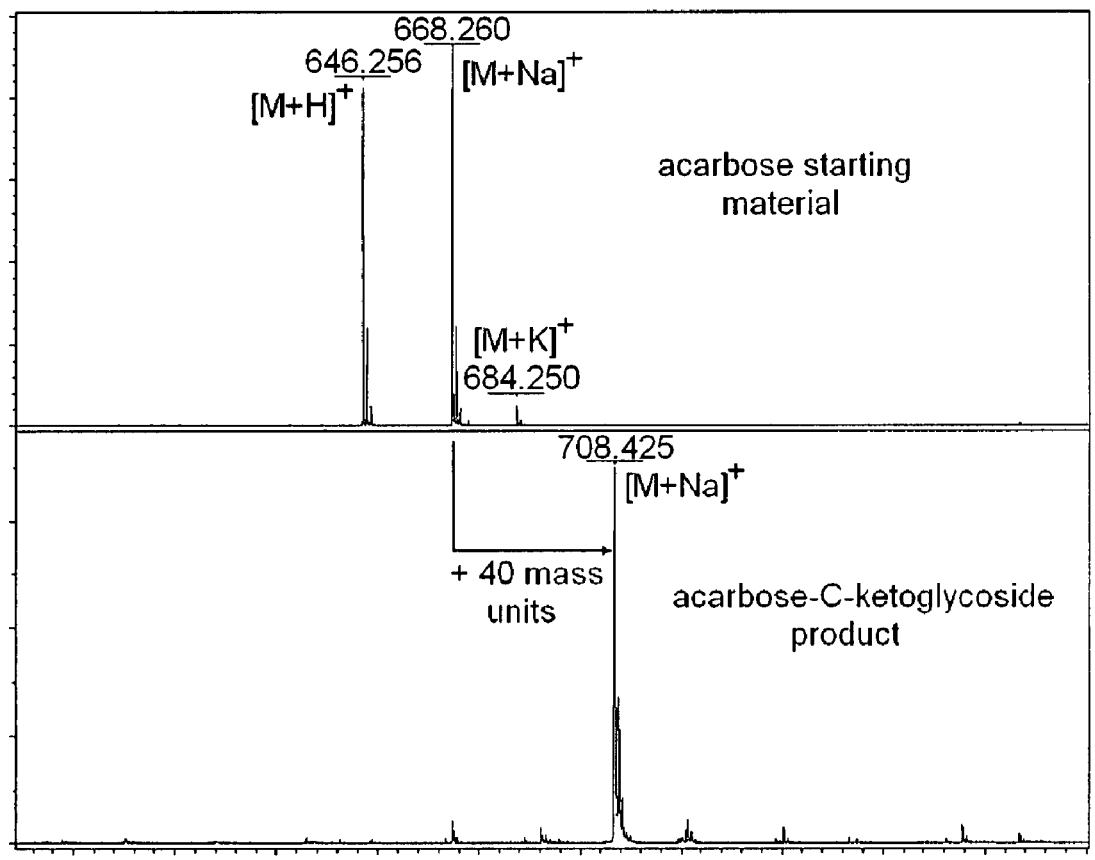
FIG. 1 shows the results of MALDI-TOF MS Analysis. The top shows the MALDI-TOF MS analysis of commercial acarbose starting material:—$[M+H]^+$, m/z 646.26 (calc. 646.25); $[M+Na]^+$, m/z 668.25 (calc. 668.25); $[M+K]^+$; m/z 684.26 (calc 684.25). Calculated monoisotopic mass $C_{25}H_{43}NO_{18}$=645.24793. the lower shows the MALDI-TOF MS analysis of acarbose "locked-ring sugar" C-ketoglycoside product:—$[M+Na]^+$, m/z 708.43 (calc. 708.4). Calculated monoisotopic mass $C_{28}H_{47}NO_{18}$=685.36.

The process of this invention is applicable to all classes of sugars that contain an aldehyde-containing aldose reducing sugar. The aldose sugar may be a simple hexose or pentose monosaccharide, or it may contain one or more substituent groups $R_1$ attached to any of the hydroxyl groups of the sugar. The $R_1$ substituents may be functional groups, including but not limited to hydroxyls, O- or N-acyls such as N- or O-acetates or O-pyruvates, acid moieties such as carboxylates, phosphates or sulfates, or O-alkyls such as O-methyl, or glycosidally linked sugars, as described in greater detail hereinbelow. Thus, the structure of most typical aldose reducing sugars (i.e., six-member ring hexoses and five-member ring pentoses) used herein may generally be represented by the structure:

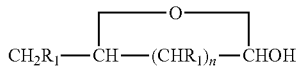

wherein n is 2 or 3, and $R_1$ at any of the C2, C3, C4, C5, and C6 carbons for hexoses, or at any of the C2, C3, C4, and C5 carbons for pentoses, are independently selected from one or more of the substituent groups described herein. When contacted with the β-diketone of the general formula:

$$CX_3-C(=O)-CX_2-C(=O)-(CX_3)_m$$

wherein m is an integer greater than or equal to one, but is preferably 1 or 2, and X at any of the noted positions is independently selected from H and a halogen, the —$CX_2$— between the ketones is acidic and reacts with the C1 of the anomeric residue of the sugar. The resultant "locked ring sugar" C-glycosidic ketone may then be shown as:

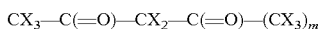

with acetic acid (or $(CX_3)_m$—COOH) also released. This C-glycosidic ketone may be reacted with a variety of ketone reactive compounds Y, which may conjugated to a solid support or detectable label $R_2$, to generate the product C-glycoside derivative of the formula:

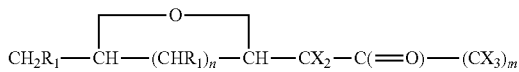

Without being limited thereto, preferred ketone reactive compounds for use herein include hydrazines ($H_2N.NH$—$R_2$) or hydrazides ($H_2N.N$—$C(=O)$—$R_2$), each of which form a stable C-glycoside ketohydrazone, hydroxylamines ($H_2NO$—$R_2$) which forms C-glycoside oximes, amines ($H_2N$—$R_2$) which form C-glycoside imines, semicarbazides ($R_2C=NNHC(=O)NH_2$) which form C-glycoside semicarbazones, and thiols (HS—$R_2$) which form C-glycoside thiolketones. $R_2$ substituents include but are not limited to solid supports for immobilization such as the wells of a microtiter plate, chips of chip-based assays, or a column, and labels such as fluorescent, enzyme or colored tags, radiolabels, biotin, Girard's reagents, or functionalized beads.

By way of example, the reaction of glucose conjugated with an $R_1$ moiety at any of the C2, C3, C4, and C6 carbons, and reacted with an $R_2$ conjugated hydrazine, the reactions may be shown as:

Reaction 1.

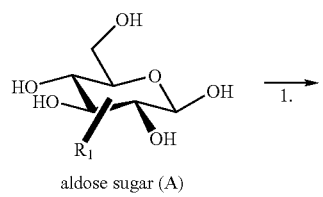

aldose sugar (A)

-continued

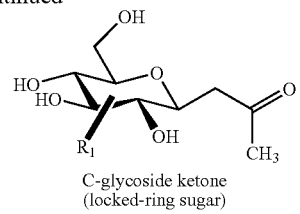

C-glycoside ketone
(locked-ring sugar)

Reaction 2

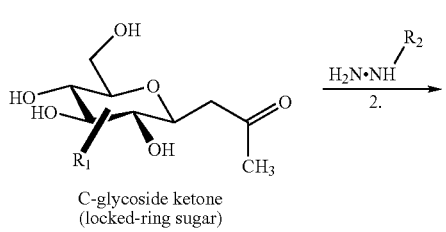

C-glycoside ketone
(locked-ring sugar)

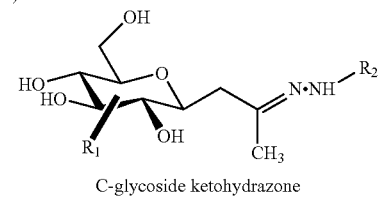

C-glycoside ketohydrazone with acetic acid and water being released as byproducts from the first and second reactions, respectively. Alternatively, for pentose sugars such as ribose, the reaction 1 may be shown as:

Reaction 1.

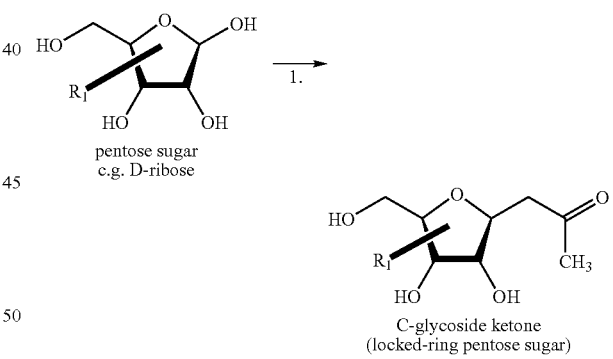

pentose sugar
e.g. D-ribose

C-glycoside ketone
(locked-ring pentose sugar)

A wide variety of aldose-containing sugars are suitable for use herein. Specific examples of monosaccharides include:

1. Neutral aldohexoses, such as D-glucose, D-mannose, D-galactose, and the less common D-allose, D-altrose, D-gulose, D-idose, D-talose. The chemistry is also applicable to the less common L-series configuration of these sugars.

2. Neutral aldopentose, such as D-ribose, D-arabinose, D-xylose, and D-lyxose, and the corresponding L-series configuration.

3. N-acylamino-aldoses, such as N-acetyl-glucosamine (GlcNAc), N-acetyl-galactosamine (GalNAc), N-acetyl-mannosamine (ManNAc), and the corresponding free amino sugars, glucosamine (GlcN), galactosamine (GalN), and mannosamine (ManN). The chemistry is equally applicable to D- and L-configurations of these sugars. Also included in the group are muramic acid (MurN) and N-acetylmuramic acid (MurNAc), both important constituents of bacterial peptidoglycan.

4. Deoxy- and deoxyamino-substituted sugars. The chemistry is applicable to:—a) the important 2-deoxyaldopentose class of sugars, such as 2-deoxyribose (dRib), 2-deoxyarabinose, and 2-deoxyxylose; b) 6-deoxy-aldohexoses, such as D- and L-fucose (Fuc), D- and L-rhamnose (Rha), and quinovose (Qui); c) the corresponding amino sugars D-/L-fucosamines (FucN), D-/L-rhamnosamines (RhaN), and D/L-quinovosamines (QuiN); d) the 2-N-acetylated 6-deoxysugars, FucNAc, RhaNAc, and QuiNAc); e) other deoxysugars of commercial importance, including 2-deoxyaldoses such as 2-deoxyglucose (dGlc) which has the 2-hydroxyl group replaced by hydrogen, so that it cannot undergo metabolic glycolysis. dGlc is therefore a good marker for tissue glucose use and hexokinase activity.

5. Methoxy-substituted sugars. The chemistry is applicable to ether-modified aldose (methoxy, ethoxy, benzyl, etc) sugars with a free anomeric position. Examples in this group are the non-metabolizable glucose analogs, 2-O-methyl-D-glucose, and 3-O-methyl-glucose, and the various partially methyl-substituted sugars used for carbohydrate linkage analysis. Others include 2-O-methylfucose, a common sugar in plant and bacterial cell walls, and 2-O-methylribose, a capping sugar for many ribonucleic acids (RNA).

6. Acidic uronic acid sugars and their salts, such as glucuronic acid (GlcA), galacturonic acid (GalA), and mannuronic acid (ManA). Also important in this category is L-iduronic acid (IdoA), a component of heparan and dermatan sulfate.

The process is also applicable to all classes of disaccharide and oligosaccharides that contain a terminal, aldehyde-containing aldose reducing sugar. Specific, non-limiting examples of oligosaccharides suitable for use as starting materials in the first reaction include:

1. Oligosaccharides derived from hydrolysis of N-linked or O-linked glycoproteins. The oligosaccharides may be detached from the glycoproteins by acid or base hydrolysis, or by enzyme-catalyzed hydrolysis, that is, by processes that generate a free reducing sugar available for formation of the C-glycoside ketohydrazones. Important examples are the N-linked oligosaccharides (N-glycans) derived from immunoglobulins (antibodies), and other glycoproteins involved in biological recognition or adherence.

2. Oligosaccharides derived from blood group antigen glycans, that determine the ABO blood type specificity. The type O antigen acceptor substrate (H antigen) is Fuc alpha1->2 Gal-. Blood types A and B have two different oligosaccharide glycolipids embedded in the cell membranes of the red blood cells. Structures of A and B antigens are GalNAc alpha1->3 (Fuc alpha1->2) Gal-, and Gal alpha1->3 (Fuc alpha1->2) Gal-, respectively. The carbohydrate moiety of the ABH and Lewis glycoproteins consists primarily of four sugars, D-galactose, L-fucose, N-acetylgalactosamine and N-acetylglucosamine. Oligosaccharide chains are attached through an alkali-labile glycosidic bond to the hydroxyl group of serine or threonine. Most of the oligosaccharide chains are linked to the backbone through an N-acetylgalactosamine residue. Specific oligosaccharide C-glycoside ketohydrazone prepared from blood group antigens may be used for the construction of diagnostic devices.

3. Oligosaccharides derived from tumor-associated antigens. Certain types of glycosphingolipids (GSL) are more highly expressed on the surfaces of tumor cells. Some of these tumor-associated antigens are adhesion molecules involved in tumor cell metastasis, tumor cell growth and motility, and have therefore been used to develop antitumor vaccines. Oligosaccharides derived from glycolipids and sphingolipids involved in adhesion and signaling are therefore targets for cancer therapy. Typical GSL antigens are the Lacto oligosaccharide series, $Le^x$, $Le^x$-$Le^x$, $Le^y$-$Le^x$, $Le^a$-$Le^a$, $SLe^x$, $SLe^x$-$Le^x$, and $SLe^a$, all of which terminate in lactose (Galbeta1->4Glc at the reducing terminus. The lactose motif is highly applicable for the formation of C-glycoside ketohydrazones. Specific oligosaccharide C-glycoside ketohydrazone prepared from tumor-associated antigens may be used for the construction of diagnostic devices for the selective detection of tumors.

4. Oligosaccharides derived from hydrolysis of bacterial peptidoglycans, lipopolysaccharides, exopolysaccharides, techioic acids, or other microbial polysaccharides. The oligosaccharides may be detached from the corresponding bacterial polysaccharide, or bacterial or microbial cells by acid or base hydrolysis, or by enzyme-catalyzed hydrolysis; i.e. by processes that generate a free reducing sugar available for formation of the C-glycoside ketohydrazones. Fluorescent, colored, biotinylated, or immobilized oligosaccharides made in this way have applications for the specific detection of pathogenic bacteria or microbes. Specifically, for the construction of diagnostic devices for the selective detection of bacteria or microbes based on their selective adherence to sugars and oligosaccharides.

5. Oligosaccharides derived from hydrolysis of glycosaminoglycans (GAGS) and proteoglycans. GAGs of physiological significance are hyaluronic acid, dermatan sulfate, chondroitin sulfate, heparin, heparan sulfate, and keratan sulfate. The linkage of GAGs to the proteoglycan core involves a specific trisaccharide composed of two galactose residues and a xylose residue (GAG-GalGalXyl-O—$CH_2$-protein). The GAGS are polysaccharides containing a repeating disaccharide unit composed N-acetylgalactosamine (GalNAc) or N-acetylglucosamine (GlcNAc) and a uronic acid such as glucuronate or iduronate, several of which are also sulfated. For example, heparan sulfate (HS) is a linear polysaccharide attached to the surface of nearly all mammalian cells. It consists of disaccharide repeats of glucuronic acid (GlcA) and N-acetyl-D-glucosamine (GlcNAc) with several modifications which can include N-deacetylation and N-sulfation of GlcNAc, epimerization of GlcA to L-iduronic acid (IdoA), 2-O sulfation of IdoA, and 6-O and 3-O sulfation of the glucosamine (GlcN). HS interact with fibroblast growth factor (FGF) and its receptor. Defective HS can cause loss of FGF and Hedgehog/Wingless signaling pathways, leading to severe abnormality in embryonic development, cell migration, and cancer cell metastasis. A well-defined physiological function of the GAG heparin is its role in preventing coagulation of the blood. In response to injury, heparin is released from the granules of mast cells that line blood vessels into the serum. Free heparin complexes with and activates antithrombin III, which in turn inhibits all the serine proteases of the coagulation cascade. This phenomenon has been clinically exploited in the use of heparin injection for anti-coagulation therapies. Specific oligosaccharide C-glycoside ketohydrazones prepared from GAGS or proteoglycans may be used for the construction of diagnostic devices, or for the suppression of blood clotting i.e. during surgery or medical procedures.

6. Other miscellaneous oligosaccharides suitable for preparation of C-glycoside ketohydrazones are a) chitin oligosaccharides; b) prebiotic oligosaccharides, such as gentiooligosaccharide (GOS), xylooligosaccharides (XOS), and cellooligosaccharides (COS); and mannan oligosaccharides (MOS); c) oligosaccharides derived from plant cell wall components, such as pectin and hemicellulose; d) oligosaccharides derived from starch or maltodextrin, which have potential as inhibitors of beta-amylase; e) acarbose, beta-amylase inhibitor. Compounds in categories d) and e) may have potential uses as antidiabetic agents.

In addition to monosaccharides and oligosaccharides, the reactions of the invention may be used for the derivatization of phosphorylated and sulfated sugars (monosaccharides, disaccharides, oligosaccharides, or nucleic acids) that contain a terminal, aldehyde-containing aldose reducing sugars that may be optionally modified by an O- or N-linked substitutent. The C-glycoside ketones and C-glycoside keto-hydrazones are readily prepared from these sugars in aqueous-based conditions and without the loss of the phosphate or sulfate groups. Specific examples include, but are not limited to:

1. Phosphorylated or sulfated monosaccharides. This includes 6-O-phosphorylated hexose monosaccharides, such as glucose-6-phosphate (Glc-6P), galactose-6-phosphate (Gal6P), N-acetylglucosamine-6-phosphate (GlcNAc-6P), mannose-6-phosphate (Man-6P), and 5-O-phosphorylated pentose monosaccharides, such as ribose-5-phosphate (Rib-5P), arabinose-5-phosphate (Ara-5P, and xylose-5-phosphate (Xyl-5P). Sulfated monosaccharides include N-acetylglucosamine-3-O-sulfate (GlcNAc-3S), and the O, N-sulfated monosaccharides such as D-GlcNSO$_3$-6OSO$_3$ and IdoA$_2$OSO$_3$ which are often found in sulfated glycosaminoglycans, such as heparin sulfate and dermatin sulfate.

2. Phosphorylated or sulfated oligosaccharides. This includes O- and N-sulfate oligosaccharides derived from hydrolysis of glycosaminoglycans (GAGS) and proteoglycans. Sulfated GAGs of physiological significance include dermatan sulfate, chondroitin sulfate, heparan sulfate, and keratan sulfate. Oligosaccharides derived from heparin sulfate of particular importance because of their anti-blood clotting activity. Phosphorylated oligosaccharides include those derived from several bacterial lipopolysaccharides. An example is alpha-L-Colp-(1-->2)-beta-D-Galp-(1-->3)-[alpha-L-Colp-(1-->4)]-beta-D-GlcpNAc, containing a 4,6-cyclic phosphate in the galactose residue. This is a phosphorylated oligosaccharide corresponding to *Vibrio cholerae O*139 polysaccharide C-glycoside ketones and C-glycoside keto-hydrazones are readily prepared from these oligosaccharides in aqueous-based conditions and without the loss of the phosphate or sulfate groups.

3. RNA- and DNA-derived oligonucleotides (aptamers). Oligonucleic acids that lack the N-linked base on the 3'-end, i.e. that terminate in a free ribose (for RNA oligos) or 2-deoxyribose (for DNA oligos) can be used to prepare C-glycoside ketones and C-glycoside ketohydrazones using the techniques described in this patent. The C-glycoside ketohydrazone chemistry is particularly applicable to labile RNA oligonucleotides. Applications of this may include the formation of fluorescent or colored oligonucleotides suitable for sequencing or in vivo hybridization technologies. RNA and DNA-derived oligonucleotide C-glycoside ketones may also be immobilized onto polymeric beads, either via biotin-avidin technologies or more directly by reaction with hydrazine- (or hydroxylamine-) functionalized beads. Immobilized aptamers bind to various molecular targets such as small molecules, proteins, nucleic acids, and even cells, tissues and organisms. This has application to DNA or RNA microarray hybridization technology that uses bead- or chip-based assays for diagnostic devices.

As noted hereinabove, the R$_2$ label group may include fluorescent, enzyme or colored tags, radiolabels, biotin, Girard's reagents, or functionalized beads. These have several major advantages over derivatization of the free aldose sugar:

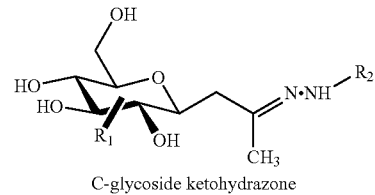
C-glycoside ketohydrazone and include:

1. The formation of the ketohydrazone in aqueous conditions, without the need for protecting group, organic solvents, or harsh reaction conditions.

2. Unlike with free sugars, the C-glycoside ketones do not react further to give osazones. This is a well-known reaction of free sugars with hydrazines that gives rise to an undesirable mixture of derivatives.

3. In contrast with most other types of sugar derivatization chemistries (such as reductive amination, or formation of reducing sugar hydrazones or oximes), the C-glycoside ketohydrazones retain the integrity of the sugar ring. The C-glycoside ketohydrazones derivatives are therefore far more likely to retain the biological properties of the parent sugar. These properties are generally lost by ring-open such as occurs during reductive amination or the formation of simple aldose hydrazones, osazones, or oximes.

Without being limited thereto, specific examples of R$_2$ labels for use herein include:

1. Fluorescent or colored R$_2$ tags. Several ketone-reactive, fluorescent or colored groups can be used to prepare stable derivatives with the C-glycoside ketones. These include the fluorescent reagents dansyl-hydrazine, fluorescein hydrazine, BODIPY-hydrazine, and Alexa Fluor hydrazine dyes, and hydrazine Cy cyanine-labeled dyes such as those used for DNA sequencing. Colored or UV-absorbent groups include the intensely red dye dabsyl hydrazine, 2,4-dinitrophenyl hydrazine, phenylhydrazine, p-nitrophenylhydroxylamine, or any other dyes functionalized with a ketone-reactive group.

2. Biotin-labeled R$_2$ tags. Biotin has the advantage of forming a strong noncovalent complex with avidin (or streptavidin). Several commercial affinity products make use of the biotin-avidin interaction. The C-glycoside ketones described in this patent react with biotin hydrazine to form a biotin labeled ketohydrazone, for example:

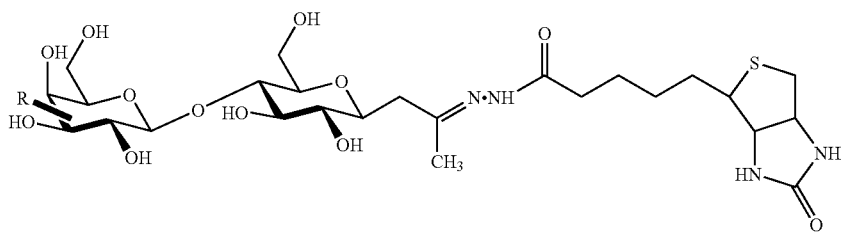

The substituent R may be any other sugar linkage, or non-carbohydrate substituents such as phosphate, sulfate, O- or N-acetate, pyruvate, O- or N-acyl. Biotin hydrazide is conjugated to the locked-ring sugar keto group, via a keto-hydrazone linkage. The water-soluble biotin motif is essentially exposed for binding with streptavidin-based products.

3. Girard's reagent $R_2$ tags. Girard's P and Girard's T reagents are hydrazides that incorporate a quaternary ammonium group. The hydrazide linkers react with the C-glycoside ketones to form stable C-glycoside ketohydrazones that carry the positively charged quaternary ammonium group:

wherein Girard's P reagent and Girard's T reagent are shown on the left and right, respectively. The hydrazine functionality (—NH.NH$_2$) reacts with the C-glycoside ketones to form stable C-glycoside ketohydrazones. The fixed positive charge on the Girard's labels have two important properties. First, they are highly sensitive to detection by positive ion-detected mass spectrometry. Hence, the Girard's-labeled C-glycoside ketohydrazones are advantageous derivatives for the mass spectrometric analysis of carbohydrates. Second, the fixed positive charge on the Girard's labels migrates towards the negative electrode during electrophoresis. Hence, the Girard's-labeled C-glycoside ketohydrazones are stable, positively-charged carbohydrate derivatives highly suitable for separation by gel electrophoresis, capillary column electrophoresis, or other forms of electrophoretic separation of carbohydrates.

4. Ketone-reactive functionalized beads. Hydrazine- or hydroxylamine-functionalized beads are commercially available in several forms (e.g., magnetically-labeled, colored, or fluorescently-labeled). These react with the described carbohydrate C-glycoside ketones to form stable ketohydrazones (or oximes with hydroxylamine beads) in which the C-glycoside ketone is covalently attached to the surface of the bead via a hydrazone linkage as follows:

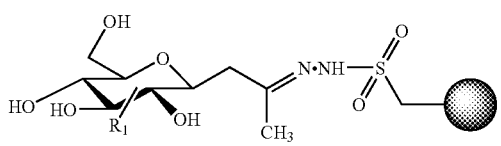

As with the other derivatives described herein, the $R_1$ substituent may be a functional group (especially a phosphate, sulfate, N- or O-acetate, O-pyruvate, or O-methyl). $R_1$ may also represent a glycosidally-linked sugar (or more than one sugar) attached to any of the hydroxyl groups, i.e., a disaccharide or an oligosaccharide.

The reaction of the aldose sugars with the β-diketone to synthesize the C-glycoside ketone Synthesis (reaction 1) is preferably performed in a buffered aqueous solvent under effective conditions and for an effective period of time. The precise conditions are somewhat variable and may be readily selected by the skilled user. By way of example, and without being limited thereto, in the preferred embodiment, the sugar is dissolved in aqueous buffer, such as sodium bicarbonate solution (38 g/L) to give a final concentration of sugar of 50 mg (0.28 mmoles) per mL. It is understood that other buffers such as potassium bicarbonate, sodium carbonate, or potassium carbonate may also be used. The pH may range from approximately 8-10, and is typically pH 8.2. A slight molar excess of acetylacetone (also called 2,4-pentanedione) is added, to typically give a final concentration of 35 mg (0.35 mmoles) per mL of buffer. Other 2,4-diketones may also be used in place of the acetylacetone, such as asymmetric 2,4-diketone or halogenated 2,4-diketones such as 1,1,1-trifluoro-2,4-pentanedione, or 1,1,1,5,5,5-hexyluoro-2,4-pentadione. The quantity of the 2,4-diketone relative to the sugar is not critical and may be increased without adversely affecting the yield of the C-glycoside ketone. The reaction may be conducted with or without heating, in any convenient reaction vessel. In one embodiment, the reaction is heated in a sealed tube, or in scaled up reactions is heated under reflux with stirring. The temperature for the synthesis may range from approximately 10-99° C. Typically, approximately 80-90° C. is preferred with a reaction time of 4 hours. However, lower temperatures are still effective but may simply require longer reaction times, and they may even be preferred for reactions involving labile sugars.

After cooling, the C-glycoside ketone product may be recovered from the reaction solution. The reaction solution may first be optionally extracted with ethyl acetate or other water-immiscible solvent in order to recover any excess 2,4-diketone. The bicarbonate (or carbonate) in the aqueous phase may be neutralized to approximately pH 7 by addition of sufficient strong cation exchange resin (typically Dowex 50 W). After removing the spent Dowex resin by filtering or allowing it to settle out, the C-glycoside ketone product can be recovered from the aqueous reaction medium by evaporation or drying. The C-glycoside ketone products are sufficiently pure (MALDI-TOF MS, NMR, GC-MS, TLC) so as not to require any chromatographic cleanup. This reduces the cost of production considerably, and indicates that scale-up to Kg quantities or greater will not present a major problem.

The C-glycoside ketohydrazones or other derivatives are prepared from the corresponding C-glycoside ketone. For this purpose, either the C-glycoside ketone can be redissolved in water, or the Dowex-neutralized aqueous reaction medium from Reaction 1 can be used directly. Preparation of the ketohydrazone requires approximately a molar equivalence or a slight molar excess of the $R_2$ hydrazine or hydrazide.

The $R_2$-hydrazine or other ketone reactive compound plus the C-glycoside are reacted, preferably with stirring, from approximately 10-99° C. for approximately 1-24 hr. Reaction at room temperature for 2 hours is typical. If necessary any excess hydrazine or other ketone reactive reagent can be removed by extraction with a water-immiscible ketone such as 1-heptanone or methyl isobutyl ketone (MIBK). The C-glycoside ketohydrazone or corresponding C-glycoside derivative is typically recovered in near-quantitative yield by evaporation of the aqueous reaction mixture.

For reactions involving functionalized beads, the corresponding product bead-labeled C-glycosides are recovered either by filtration, centrifugation, or by settling out, and are washed free of any un-reacted reagents by washing with an aqueous nonionic detergent (e.g., 1% TRITON X-100), and subsequently with several washes of water.

The following examples are intended only to further illustrate the invention and are not intended to limit the scope of the invention which is defined by the claims.

Example 1

Acarbose is a tetrasaccharide starch analog produced by fermentation from *Streptomyces*, that is used orally for the treatment of Type 2 diabetes and pre-diabetes. X-ray crystallography and NMR studies have established that acarbose is a potent competitive inhibitor of human alpha-amylase. Complexation to acarbose depletes the active alpha-amylase in saliva, so that there is less available to degrade starch from ingested food. This leads to a lowering of the total blood glucose that is usually derived from starch, and is important in controlling glucose homostatus.

A non-hydrolyzable C-ketoglycoside was produced from acarbose. The C-ketoglycoside group is introduced into the acarbose molecule at the anomeric position of the terminal glucose reducing sugar to form a conformationally-locked pyranose ring, called a "locked-ring sugar".

where A shows the structures of acarbose, and B shows the acarbose "locked-ring sugar" C-ketoglycoside. The sugar residues are assigned I, Ia, II, III, and IV. The reactive ketone group is boxed.

The acarbose "locked-ring sugar" C-ketoglycoside was prepared from acarbose (obtained commercially from Toronto Research, Toronto, Canada) and acetylacetone in aqueous-based reaction as described before. Acarbose (50 mg, 0.77 mmoles) was dissolved in aqueous sodium bicarbonate buffer (2 mL, 38 mg/mL, pH 8.2). To this was added acetylacetone (100 microliters). The mixture was heated in a sealed reaction tube for 4 hours at 80° C. After this time the reaction was cooled to room temperature and neutralized by addition of Dowex 50W strong anion exchanger. The neutralized mixture was extracted with ethyl acetate to remove any excess acetylacetone. The yield and purity were determined by matrix-assisted laser desorption/ionization time-of-flight mass spectrometry (MALDI-TOF MS) and by gas chromatography-mass spectrometry (GC-MS). See FIG. 1. The yield of acarbose "locked-ring sugar" C-ketoglycoside based on ion peak height percentage ratios, was m/z 708.43/668.25× 100=>97%.

Figure 2:
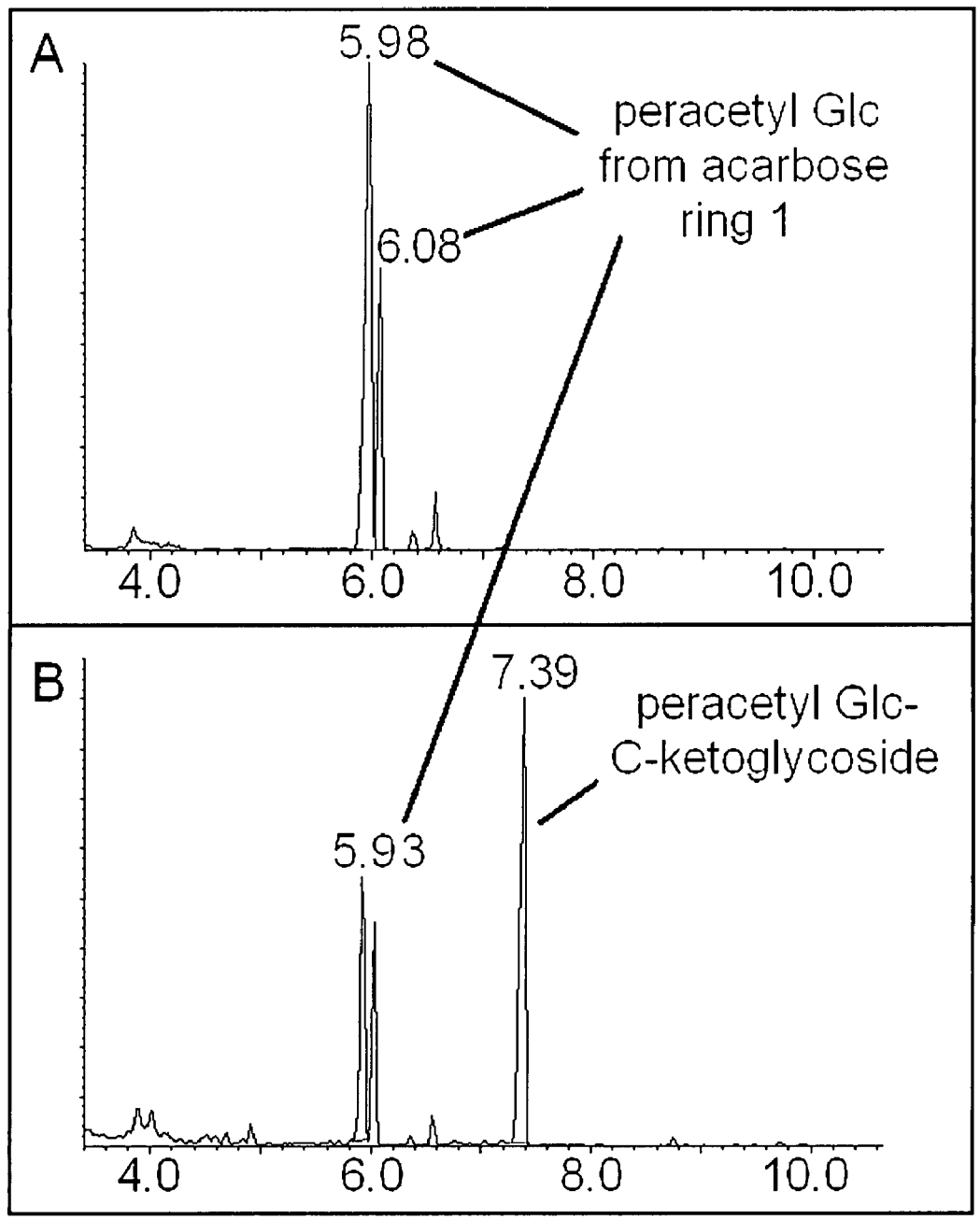
FIG. 2 shows the GC-MS analysis of (A.) acarbose prior to reaction and (B.) acarbose-C-ketoglycoside after hydrolysis with trifluoroacetic acid, and peracetylation. Note evidence for the C-ketoglycoside ring (ring 1a as defined in FIG. 1) at RT 7.9 min.
Figure 3:
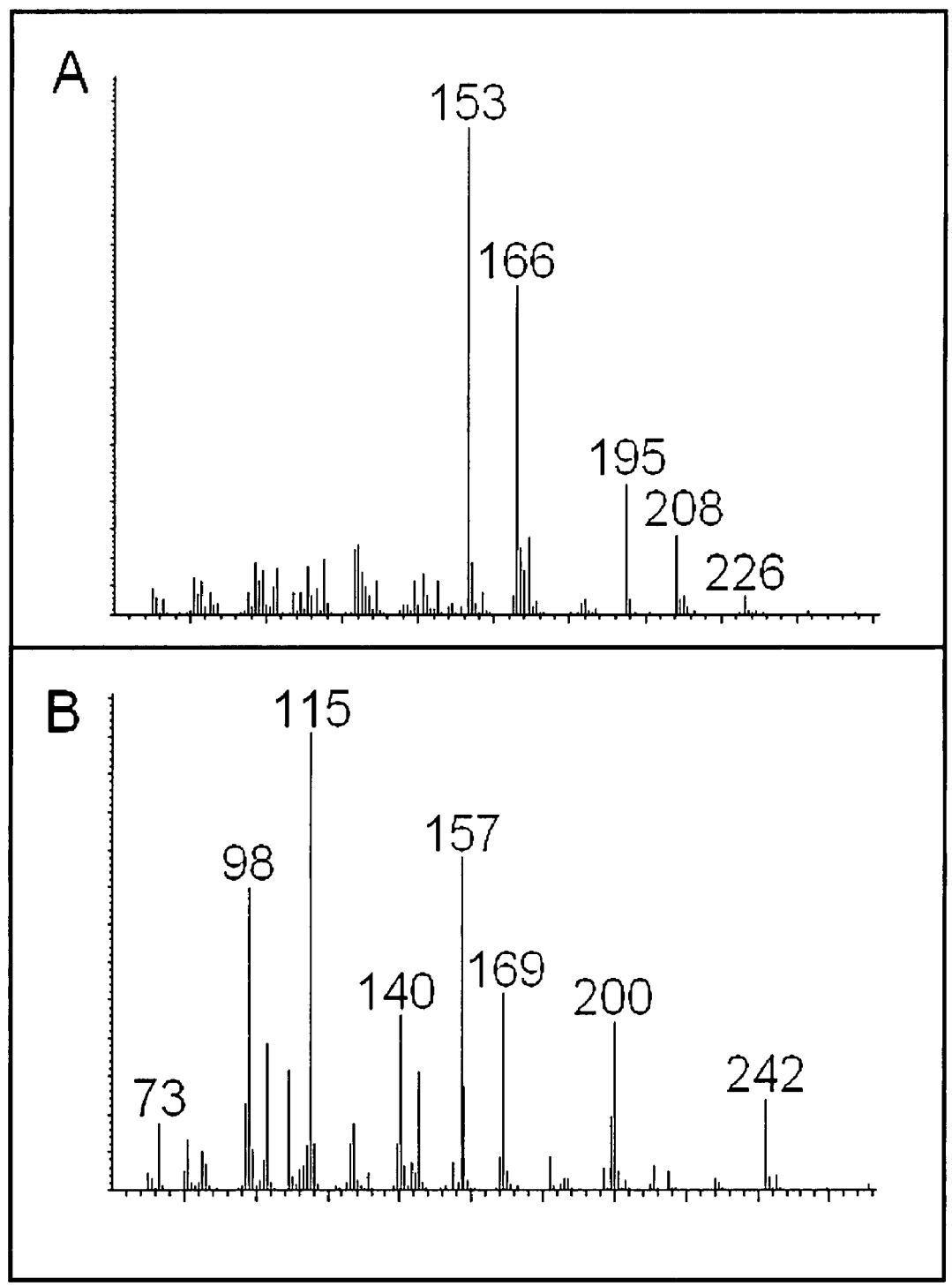
FIG. 3A (top) shows the mass spectrum for Peak at 7.39 mins (peracetylated Glc-C-glycoside).
FIG. 3B (lower) shows the mass spectra for peaks at 5.98 min and 6.08 min, due to alpha- and beta-peracetylated glucose.

GC-MS analysis of component monosaccharides was conducted following trifluoroacetic acid hydrolysis (aqueous TFA, 2.0M, 90° C., 1 h), and peracetylation (50:50 acetic anhydride:pyridine, 90° C., 1 h). The peracetylated component monosaccharides were partitioned between ethyl acetate and water prior to analysis by GC-MS. The results are shown in FIGS. 2 and 3.

Acarbose-C-ketoglycoside immobilized on p-toluenesulfonylhydrazine-functionalized polymer resin beads is prepared via a covalent ketohydrazone linkage. The reactive ketone group in the C-ketoglycoside side chain is available for conjugation with ketone-reactive groups, such as a hydrazine-based, or oxime-based, or amine-based, or semicarbazone-based linker.

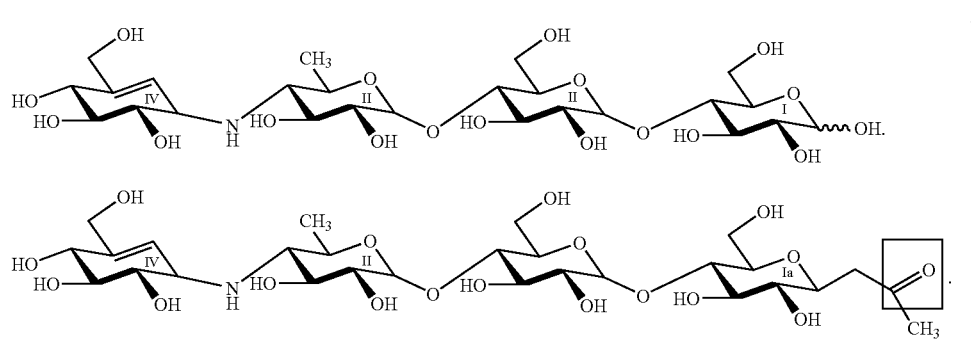

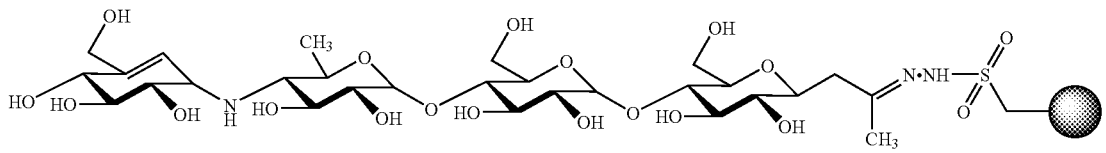

The acarbose-C-ketoglycoside (50 mg) prepared as described above was shaken in aqueous solution (room temperature, 18 h) with p-toluenesulfonylhydrazine (p-TSH) polymer-bound beads (100 mg, 100-300 mesh, 1% cross-linked) obtained from Sigma-Aldrich Chemicals, St. Louis, USA). Stated PTSH loadings were 1.5 mmol/g (Aldrich product no. 53,233-9) and 2.5 mmol/g (Aldrich product no. 53,232-0). After 18 h, the resins were allowed to settle out under gravity and the supernatant was removed by decanting. The beads were washed by vortexing with water (6×3 mL), once with aqueous nonionic detergent (2% Triton X-100, 3 mL), and then sufficient times with water to ensure complete removal of the detergent (i.e. typically 10 more times). The washed beads were air dried and stored at room temperature.

Figure 4:
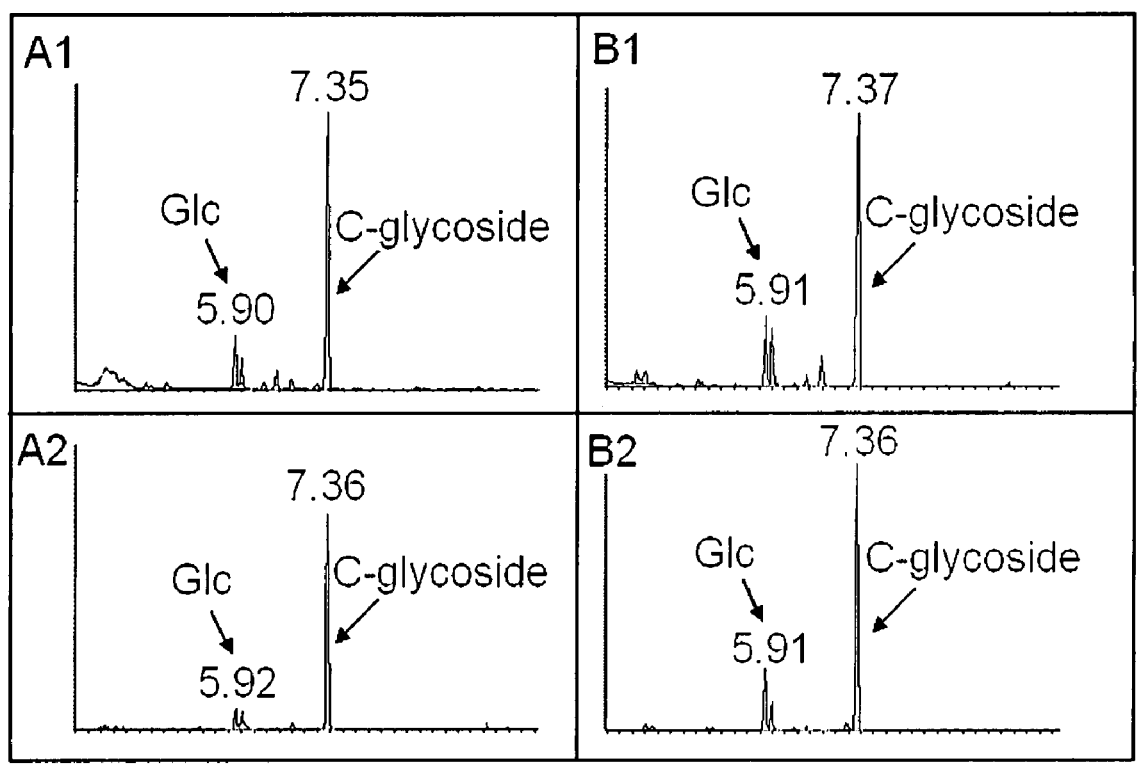
FIG. 4 shows the GC-MS analysis of the acid-catalyzed removal of sugars from Acarose-functionalized beads. A1: 1.5 mMol beads after 6× water wash; A2: as A1, but with a subsequent wash with non-ionic detergent (2% Triton X-100, plus 10× water). B1: 2.5 mMol beads after 6× water wash; B2: as B1, but with a subsequent wash with non-ionic detergent (2% Triton X-100, plus 10× water). The beads both have the Glc-C-glycoside (from acarbose ring Ia) and Glc (from acarbose ring 2) after TFA hydrolysis and peracetylation.

The detergent-washed functionalized beads (about 5 mg) were treated with trifluoroacetic acid (2M, 90° C., 1 h) to hydrolyze the acarbose-C-ketoglycoside covalently attached to their surface. Following removal of the TFA by evaporation, the residue was peracetylated by treatment with acetic anhydride and dry pyridine (2 mL, 1:1 vol/vol, 90° C., 1 h). The peracetylated monosaccharides were recovered by partitioned between ethyl acetate and water and analyzed by GC-MS. See FIG. 4.

Figure 5:
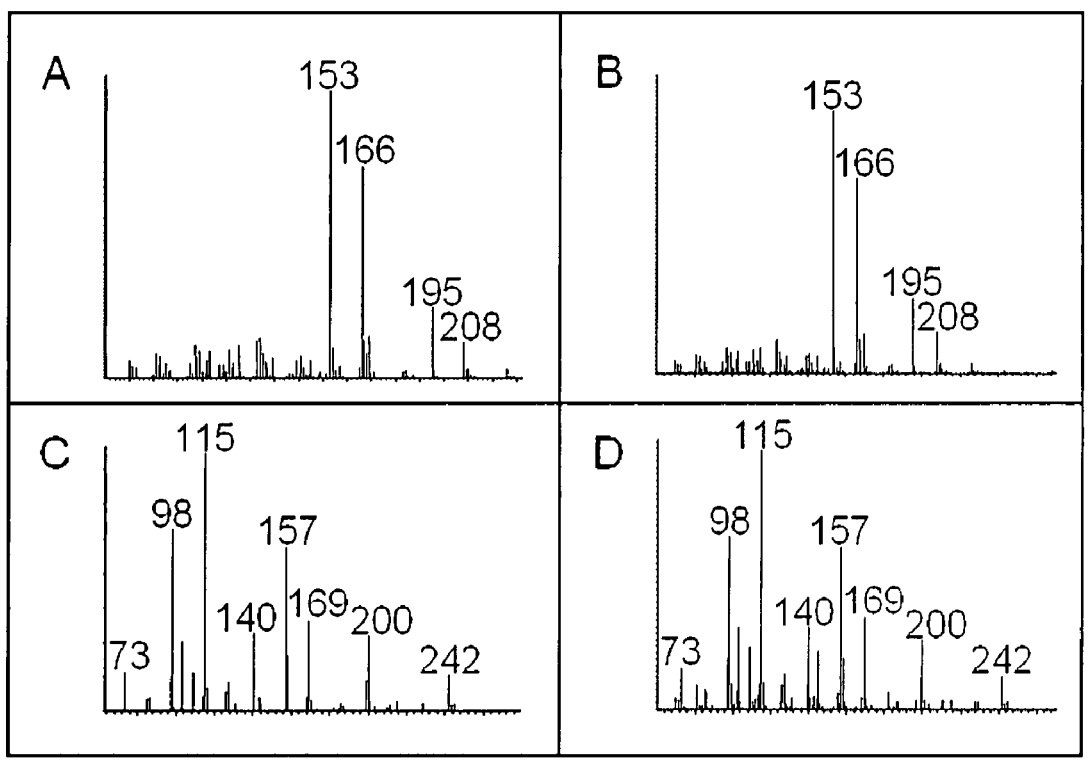
FIG. 5 shows the mass spectrometry evidence of the covalent attachment of the acarbose-C-ketoglycoside to the hydrazine-functionalized beads. The acarbose-C-beads (A. 1.5 mmol/g loading, B. 2.5 mmol/g loading) were water-washed (×6), Triton X-100 washed (2% aqueous), and again water washed (×10). The washed beads were acid hydrolyzed and peracetylated, and the sugars released were analyzed by GC-MS. Panels A and B are the spectra of the Rt 7.3 min GC peaks (see FIG. 4) arising from the acarose terminal Glc-C-glycoside (i.e. ring Ia). Panels C and D are spectra of the 5.9 min GC peaks arise from the released Glc (i.e. acarbose ring II) For reference, compare with the spectra in FIG. 3.

The chromatographs and mass spectra of the TFA-hydrolyzed material from the acarbose-functionalized beads was identical with the those obtained for acarbose "locked-ring sugar" C-ketoglycoside. The analysis of the TFA-hydrolyzed beads (both 1.5 mmol/g and 2.5 mmol/g loadings) revealed two GC-MS peaks corresponding to at Rt 5.91 min and 6.02 min, that are assigned as peracetylated alpha- and beta-glucose from glucose Ring II, and a third peak at Rt 7.37 min assigned as glucose-C-ketoglycoside arising from Ring Ia. The latter peak (Rt 7.37 min) gave rise to a EI-MS spectrum composed of four major ions m/z 153, 166, 195, and 198, that are characteristic for peracetylated glucose-C-ketoglycoside (Price, Momany, Adeuya. Carbohydr. Res. In preparation). As assessed by the relative areas of the GC peaks Rt 7.37 min, the immobilized acarbose-C-ketoglycoside attached at the different bead loadings (1.5 mmol/g and 2.5 mmol/g) were similar, with an observed ratio of 4.0:6.5, respectively. The results are shown in FIG. 5.

These acarbose-functionalized beads have expected applications for affinity purification, affinity chromatography, or affinity precipitation of alpha-amylase, a key protein of diabetic starch metabolism. The acarbose-functionalized beads have potential for proteomic analysis of human saliva starch-binding proteins as a diagnostic tools for diabetes mellitus or pre-diabetes.

It is understood that the foregoing detailed description is given merely by way of illustration and that modifications and variations may be made therein without departing from the spirit and scope of the invention.

I claim:

1. A method for preparing sugar C-glycoside derivatives comprising:
    a) reacting an aldose reducing sugar with a β-diketone under conditions and for a period of time effective to form a C-glycoside ketone, which said aldose reducing sugar comprises an aldehyde containing hexose aldose reducing sugar or an aldehyde containing pentose aldose reducing sugar, wherein said hexose is optionally substituted at one or more of the C2, C3, C4, C5, and C6 positions thereof and said pentose is optionally substituted at one or more of the C2, C3, C4, and C5 positions thereof, and
    b) reacting said C-glycoside ketone with a ketone reactive compound, which said ketone reactive compound is optionally linked to a detectable label or solid surface, under conditions and for a period of time effective to form a C-glycoside derivative wherein said ketone reactive compound is conjugated at the carbon of the ketone of said C-glycoside ketone, and the ring structure of said sugar remains intact, wherein said ketone reactive compound is selected from the group consisting of hydrazines or hydrazides, semicarbazides, and thiols, and said C-glycoside derivative is selected from the group consisting of C-glycoside ketohydrazones, C-glycoside semicarbazones, and C-glycoside thiolketones, respectively.

2. The method of claim 1 wherein said reacting an aldose reducing sugar with a β-diketone and said reacting said C-glycoside ketone with a ketone reactive compound are both conducted in an aqueous solvent.

3. The method of claim 2 wherein said reacting an aldose reducing sugar with a β-diketone is conducted in the presence of a buffer.

4. The method of claim 1 wherein said detectable label is selected from the group consisting of fluorescent markers, enzymes, radiolabels, colored markers, biotin, Girard's reagents, and beads.

5. The method of claim 1 wherein said hexose is independently substituted at one or more of the C2, C3, C4, C5, and C6 positions thereof, and said pentose is independently substituted at one or more of the C2, C3, C4, and C5 positions thereof, with a moiety selected from the group consisting of O-acyls, N-acyls, acid moieties, carboxylates, phosphates, sulfates, N-acetates, O-acetates, O-pyruvates, O-alkyls, and glycosidically-linked sugars.

6. The method of claim 1 wherein said aldose reducing sugar is a monosaccharide selected from the group consisting of neutral aldohexoses, neutral aldopentoses, -acylamino-aldoses, deoxy-substituted sugars, deoxyamino-substituted sugars, methoxy-substituted sugars, and acidic uronic acid sugars and their salts.

7. The method of claim 1 wherein said aldose reducing sugar comprises a disaccharide or oligosaccharide.

8. The method of claim 7 wherein said aldose reducing sugar is selected from the group consisting of oligosaccharides derived from the hydrolysis of N- or O-linked glycoproteins, oligosaccharides from blood group antigen glycans that determine ABO blood type specificity, oligosaccharides from glycosphingolipids, oligosaccharides derived from the hydrolysis of microbial polysaccharides, bacterial peptidoglycans, bacterial lipopolysaccharides, bacterial exopolysaccharides, and bacterial techioic acids, oligosaccharides derived from the hydrolysis of glycosaminoglycans and proteoglycans, chitin oligosaccharides, xylooligosaccharides, mannan oligosaccharides, oligosaccharides derived from pectin and hemicellulose, oligosaccharides derived from starch or maltodextrin, and acarbose.

9. The method of claim 1 wherein said aldose reducing sugar comprises a phosphorylated or sulfated sugar.

10. The method of claim 9 wherein said aldose reducing sugar is selected from the group consisting of phosphorylated or sulfated monosaccharides phosphorylated or sulfated oligosaccharides, and oligonucleotides from RNA or DNA which lack the N-linked base at the 3' end.

11. The method of claim 1 wherein said ketone reactive compound is selected from the group consisting of hydrazines and hydrazides, and said C glycoside derivative is a C-glycoside ketohydrazone.

12. The method of claim 1 wherein said reacting said C-glycoside ketone with a ketone reactive compound produces a product which consists essentially of said C-glycoside derivative wherein said ketone reactive compound is conjugated at the carbon of the ketone of said C-glycoside ketone, and the ring structure of said sugar remains intact.

13. The method of claim 1 wherein said C-glycoside derivative is produced from said reacting said C-glycoside ketone with a ketone reactive compound in an approximate quantitative yield.

* * * * *